United States Patent [19]

Esanu

[11] 4,254,162

[45] Mar. 3, 1981

[54] PHENOXY ACETIC ACID DERIVATIVE, ITS PREPARATION AND THERAPEUTIC USE

[75] Inventor: Andre Esanu, Paris, France

[73] Assignee: Societe d'Etudes de Produits Chimiques, Paris, France

[21] Appl. No.: 97,037

[22] Filed: Nov. 21, 1979

Related U.S. Application Data

[63] Continuation of Ser. No. 897,287, Apr. 17, 1978.

[30] Foreign Application Priority Data

Apr. 22, 1977 [GB] United Kingdom ............... 16789/77

[51] Int. Cl.³ ............................................. A61K 31/38

[52] U.S. Cl. .................................................. 424/275

[58] Field of Search ......................................... 424/275

[56] References Cited

U.S. PATENT DOCUMENTS 4,017,632   4/1977   Thuillier et al. ...................... 424/275

*Primary Examiner*—Frederick E. Waddell
*Attorney, Agent, or Firm*—Eyre, Mann, Lucas & Just

[57] ABSTRACT

A therapeutic use for a phenoxy acetic acid is disclosed. The compound is effective as a choleretic agent and can be administered orally or intravenously.

6 Claims, No Drawings

PHENOXY ACETIC ACID DERIVATIVE, ITS PREPARATION AND THERAPEUTIC USE

This is a continuation of application Ser. No. 897,297, filed Apr. 17, 1978.

This invention relates to a new phenoxy acetic acid derivative, to a method for its preparation and to therapeutic compositions containing it.

The new derivative of this invention is [2-isopropyl-4-(2-thenoyl)-5-methyl]-phenoxy acetic acid, which has the formula:

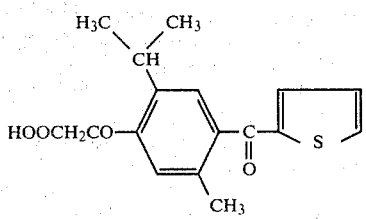

The new compound has the general formula $C_{17}H_{18}O_4S_1$ and has a molecular weight of 318. It is a white crystalline product melting at 147°–148° C. (Tottoli), and insoluble in water, soluble in ethanol, chloroform, dimethylsulphoxide and transcutanol.

The compound is particularly interesting for its therapeutic activities in the field of choleresis. It may be used as such per os or under the form of its soluble salts with alkali metals for intravenous administration.

A toxicity study undertaken on this compound has given per os LD 50 figures of about 0.8 g. per kilo for female mice and 2.35 g/kg. for female rats. Sodium and potassium salts are a little less toxic.

Complete comparative pharmacological studies (on rats) undertaken, for the choleresis, on the compound of this invention and on sodium dehydrocholate, have shown a very favourable activity of the compound of this invention, with respect to the reference compound.

The technic used was that one described in J. Pharmacologie, Paris, 1971, 2, 2, 175–182 on anaesthesied famale rats; in this experimentation were determined 1, 2, 3 and 4 hours later per os administration for treated rats compared with non-treated rats, the percentage of variation of bile flow (A), the percentage of variation of amount of protein in the bile flow (B) and the percentage of variation of cholesterol amount (C).

A first batch of 10 rats was anaesthesied and zero time taken 15' after the anaesthesy; 1, 2, 3 and 4 hours later were measured the bile flows, the amounts of protein and cholesterol; the average figures obtained were retained as a basis for comparison.

Similar measures were thus made for 4 batches of each 6 rats treated per os by 4 different doses of the compound of the invention and, in each case, the percentage of variation was calculated with respect to the corresponding values of non-treated animals.

The same work was then done with 3 batches of each 6 rats treated by 3 different doses of sodium dehydrocholate and the calculated figures obtained for both experimentations were reported in the accompanying table.

For sodium dehydrocholate doses retained were the generally accepted one of 100 mg/kg, one lower and one higher.

For the compound of the invention, preliminary tests having lead to the figures of 25 and 50 mg/kg as favourable doses, one lower and one higher doses were also retained for safety purposes.

The compound according to the invention does not induce the liberation of cholesterol at a high rate; this is nevertheless an advantage as demonstrated by the publication FEUILLETS DE BIOLOGIE, 1977-Vol. XVIII-N° 97-page 65 to 70.

Turning now to the form of administration, for oral route, tablets and gelatine capsules are preferred; each unit may comprise from 0.05 to 0.25 g. of active ingredient, acid form; for intravenous administration, the preferred form is one alkali metal salt of the compound with a dosage of 0.25 to 0.50 g. of active ingredient per phial.

Usual posology in human administration comprises 0.05 to 0.25 g. per diem for oral route and 0.25 to 0.50 g. per diem for intravenous route.

This invention accordingly provides a therapeutic composition comprising the compound according to the invention or an alkali metal salt of the same in admixture with one or more pharmacologically acceptable diluents or carriers.

The new compound may be prepared according to this invention by reacting 2-isopropyl-4-(α-thenoyl)-5-methylphenol with ethyl monobromoacetate under reflux in a ketonic solvent. From the resulting ethyl ester, the compound of the invention may be directly obtained by hydrolysis.

2-isopropyl-4-(α-thenoyl)-5-methylphenol may be obtained by reacting thymol on thenoyl chloride in the presence of aluminium chloride in acetylene tetrachloride.

This invention is illustrated by the following example:

EXAMPLE

Into a one-liter reactor, fitted with stirring, warming and cooling means there were poured:

31.44 g. (0.12 mole) of 2-isopropyl-4-(α-thenoyl)-5-methyl phenol 400 ml. of methyl ethyl ketone 33 ml. of ethyl bromoacetate 24 g. (0.19 mole) of potassium carbonate, and some potassium iodide crystals.

The mixture was then stirred and refluxed for four hours. Then it was evaporated to dryness, extracted with 400 ml of diethyl ether, washed with water, once more evaporated to dryness and recrystallized from hexane.

There were thus obtained 38.4 g. of the ethyl ester of the compound of the invention (yield: 85%).

38.4 g (0.106 mole) of this ester, 22 g. (0.55 mole) of pure sodium hydroxide and 600 ml of ethanol were added to a one-liter reactor fitted with stirring and warming means, and then refluxed for three hours, evaporated to about 400 ml, cooled and mixed under stirring with 34 ml of acetic acid (a 10% excess).

After 30 minutes of stirring, the mixture was filtrated and the precipitate was washed and recrystallized from benzene.

There were thus obtained 28.6 g (yield: 85% of the product, [2-isopropyl-4-(α-thenoyl)-5-methyl]-phenoxy acetic acid, the structure of which was confirmed by analysis and U.V. spectrum.

Corresponding alkali metal salts are obtained from the acid by the usual routes.

| Product | Doses mg/kg | 1 hour | | | 2 hours | | | 3 hours | | | 4 hours | | |
|---|---|---|---|---|---|---|---|---|---|---|---|---|---|
| | | A | B | C | A | B | C | A | B | C | A | B | C |
| Product of the invention | 12.5 | +42 | +59 | −17 | +16 | +2 | +8 | +10 | −13 | −3 | +10 | +13 | +3 |
| | 25.0 | +52 | +58 | +35 | +26 | +40 | +27 | +13 | +7 | +10 | +6 | +16 | +10 |
| | 50.0 | +62 | +77 | −1 | +49 | +50.5 | +24 | +30 | +36 | +18 | +21 | +26 | −1 |
| | 75.0 | +87 | +103 | — | +75 | +78 | — | +60 | +56 | — | +44 | +47 | — |
| Sodium dehydrocholate | 50.0 | +33 | +24 | +14 | +16 | +10 | +7.5 | +11 | +5 | +9.5 | +7 | −2 | +4 |
| | 100.0 | +77 | +50 | +10 | +18 | +20 | −2 | +7 | +5.5 | +4 | +6 | +36 | +8 |
| | 150.0 | +144 | +98 | — | +48 | +32 | — | +23 | +11 | — | +2 | +11 | — |

I claim:

1. A method of treating choleresis comprising the oral administration of a therapeutic composition comprising a choleretically effective amount of a compound selected from the group consisting of [2-isopropyl-4-(2-thenoyl)-5-methyl]-phenoxy acetic acid and alkali metal salts thereof together with a pharmaceutically acceptable carrier therefor.

2. The method of claim 1 wherein the therapeutic composition is administered as a tablet or capsule having from 0.05 to 0.25 gram of the said compound.

3. The method of claim 2 wherein the said compound is in the acid form.

4. A method of treating choleresis comprising the intravenous administration of a therapeutic composition comprising a choleretically effective amount of a compound selected from the group consisting of 2-isopropyl-4-2(thenoyl)-5-methyl-phenoxy acetic acid and alkali metal salts thereof together with a pharmaceutically acceptable carrier therefor.

5. The method of claim 4 wherein the therapeutic composition is administered intravenously with a dosage of 0.25 to 0.5 gram of said compound per phial.

6. The method of claim 5 wherein the said compound is in the form of an alkali metal salt.

* * * * *